(12) United States Patent
Schrag

(10) Patent No.: US 8,545,385 B2
(45) Date of Patent: Oct. 1, 2013

(54) IMPLANTABLE RESERVOIR BODY

(75) Inventor: Hans-Juergen Schrag, Friedenweiler (DE)

(73) Assignee: Dritte Patentportfolio Beteilgungsgesellschaft mbH & Co. KG, Schönefeld/Waltersdorf (DE)

( * ) Notice: Subject to any disclaimer, the term of this patent is extended or adjusted under 35 U.S.C. 154(b) by 422 days.

(21) Appl. No.: 12/937,887

(22) PCT Filed: Jan. 30, 2009

(86) PCT No.: PCT/DE2009/000138
§ 371 (c)(1),
(2), (4) Date: Oct. 14, 2010

(87) PCT Pub. No.: WO2009/127176
PCT Pub. Date: Oct. 22, 2009

(65) Prior Publication Data
US 2011/0034757 A1 Feb. 10, 2011

(30) Foreign Application Priority Data
Apr. 15, 2008 (DE) .......................... 10 2008 018 797

(51) Int. Cl.
*A61F 2/00* (2006.01)
(52) U.S. Cl.
USPC .......................................................... 600/29
(58) Field of Classification Search
USPC .............................. 600/29–32; 128/897–899
See application file for complete search history.

(56) References Cited

U.S. PATENT DOCUMENTS

| 2005/0250979 | A1 | 11/2005 | Coe |
| 2007/0213580 | A1 | 9/2007 | Schrag |
| 2008/0143619 | A1 | 6/2008 | Wotherspoon |

FOREIGN PATENT DOCUMENTS

| DE | 19845292 A1 | 5/1999 |
| DE | 10013519 A1 | 10/2001 |
| DE | 102004018807 A1 | 11/2005 |
| DE | 60116599 T2 | 11/2006 |
| EP | 1886628 A2 | 2/2008 |
| FR | 2756485 A1 | 6/1998 |

OTHER PUBLICATIONS

Int'l Search Report issued on Jun. 9, 2009 in Int'l Application No. PCT/DE2009/000138.
Response dated Oct. 12, 2009 to Written Opinion in Int'l No. Application No. PCT/DE2009/000138 with English translation.
Int'l Preliminary Report on Patentability issued on Mar. 13, 2010 in Int'l Application No. PCT/DE2009/000138.
Office Action issued Jan. 15, 2009 in German Appln. Ser. No. 10 2008 018 797.6-35.
Translation of Int'l Preliminary Report on Patentability issued on Mar. 13, 2010 in Int'l Application No. PCT/DE2009/000138.
Office Action issued Jan. 26, 2012 in DE Application No. 10 2008 018 797.6.

*Primary Examiner* — John Lacyk
(74) *Attorney, Agent, or Firm* — Panitch Schwarze Belisario & Nadel LLP

(57) ABSTRACT

An implantable reservoir body is provided which, as and when required, makes available a working medium that serves at least to inflate an implantable unit. An elastic hollow body is provided whose wall encloses a reservoir volume, and an induction coil arrangement is provided inside the reservoir volume and/or an induction coil arrangement is connected to the wall of the hollow body. The induction coil arrangement is connected to a pump/electronics unit provided inside or outside the hollow body, and a fluid channel is provided which leads out of the hollow body and which is connected to the pump unit and/or directly to the implanted unit that is to be inflated.

11 Claims, 3 Drawing Sheets

IMPLANTABLE RESERVOIR BODY

CROSS-REFERENCE TO RELATED APPLICATIONS

This application is a Section 371 of International Application No. PCT/DE2009/000138, filed Jan. 30, 2009, which was published in the German language on Oct. 22, 2009, under International Publication No. WO 2009/127176 A1 and the disclosure of which is incorporated herein by reference.

BACKGROUND OF THE INVENTION

The invention relates to an implantable reservoir body for the demand-oriented supply of a working medium which serves at least for inflating an implantable unit.

PRIOR ART

Implantable reservoir bodies serve for the intracorporeal supply of an implantable actuator working on the basis of the hydrodynamic or pneumatic principle of action with a working medium which is transferred to or infiltrated into a filling volume on the actuator side via a fluid or transmission line for directed actuating of the actuator, or, in a reverse manner, is transferred back to the reservoir body from the filling volume on the actuator side. The exchange of the working medium between the reservoir body and the filling volume on the actuator side is performed by a miniaturized pump unit which is activated upon demand via a control electronics module.

Some specific application and realization examples will be mentioned hereinafter as representative for a plurality of reservoir body systems.

German published patent application DE 198 45 292 A1 describes a device for treating incontinence, i.e., the incapability of holding urea or stool, which may assist or even replace the natural organ activity by a micropump-controlled compression of the urethra or anus by an implant around the respective organ of variable inner diameter. The device is in this case composed of a reservoir body that may be freely placed within the body and is connected to an actuator implemented as a compression ring via a fluid or transmission line. Along this transmission line a micropump unit is provided, the micropump action of which and the filling level of the compression ring associated therewith through a transcutaneous energy supply of the micropump may be determined by a user-selectable period of time.

A further example of the application of an implantable reservoir body is known from German published patent application DE 100 13 519 A1, in which an implantable sphincter prosthesis is described. For a controllable constriction of the urethra, the prosthesis comprises a collar with an inflatable body attached thereto, which can block the urethra by way of a dilation. Via a hose conduit, the inflatable body is connected to a reservoir body realized as a flexible vessel, in which a saline solution is stored as a working medium. A pump unit including a control and supply and appropriately conveying the saline solution is provided along the hose conduit, which is applied subcutaneously under the skin so as to enable an inductive energy and signal exchange between the supply and control device, which can be positioned to be extracorporeal, and the implantable pump unit.

A further example of application of an implantable reservoir body can be derived from German Patent DE 10 2004 018 807 B4, in which an implantable sphincter prosthesis system is described, which provides for a compression cuff attached to the inner side of an elastic support ring as well as an elastic, so-called reservoir cuff attached to the outside of the support ring. The two hollow bodies, each consisting of an elastic material that can be evacuated, are connected to each other via a micropump, which conveys a transmission fluid back and forth between the two hollow bodies depending on the degree of compression of the compression cuff.

All such systems to be implanted are governed by the demand for a design which is as compact and space-saving as possible and which by way of implantation should not cause any, or only the most minor, possible irritations in the patient, although the goal is to optimize the functionality, efficiency and ultimately the lifetime of such systems. In this respect, the reservoir body to be implanted, from which the working medium required for the desired actuator performance from an implanted unit is to be provided in a controlled manner for purposes of a metered inflating of the filling volume on the actuator side, is of particular importance. Due to a mostly cyclic operating mode of an actuator unit to be implanted, it is likewise required to guarantee a controlled reflow of the working medium into the reservoir body for purposes of deflating the filling volume on the actuator side.

BRIEF SUMMARY OF THE INVENTION

The invention is based on the object of providing an implantable reservoir body for the demand-oriented supply of a working medium, which serves at least for inflating an implantable unit, optimized with respect to shape, size and functionality, so as to reduce to a minimum the irritations caused in a patient by the implantation. Furthermore, an implantable reservoir body should be enabled to be formed largely independent of the functionality of the implantable unit to be operated by the working medium, so that the most modular use possible of the reservoir body, respectively a free combinability of the reservoir body with implantable units of largely different configurations should be possible.

A solution to the task on which the invention is based comprises an implantable reservoir body for the demand-oriented supply of a working medium serving at least for inflating an implantable unit, wherein the implantable reservoir body is connected to at least one inflatable and implantable unit, characterized in that an elastic hollow body is provided, the hollow body wall of which encloses a reservoir volume, that an induction coil arrangement is provided within the reservoir volume and/or an induction coil arrangement is connected to the hollow body wall, that the induction coil arrangement is connected to a pump/electronics unit provided inside or outside the hollow body, and that a fluid channel is provided which leads out of the hollow body and is connected to the pump unit and/or directly to the implanted unit to be inflated.

The features further developing the idea behind the invention in an advantageous manner can be derived from the further description, in particular with reference to the illustrated exemplary embodiment.

The implantable reservoir body according to the invention is based on the idea of integrating an induction coil arrangement, required for the supply of electric energy as well as the advantageous exchange of electric signals, within the reservoir body. Thus, an elastic hollow body is provided, the hollow body wall of which encloses the reservoir volume, wherein the induction coil arrangement is positioned within the reservoir volume and/or the induction coil arrangement or a further induction coil arrangement is connected to the hollow body wall or integrated into the hollow body wall. Due to such a combination of reservoir body with at least one induction coil arrangement, the mostly flat shape of the reservoir body is used in an advantageous manner in order to accommodate the likewise flat-formed induction coil arrangement in a space-saving manner in the form of one or more flatly spread electric windings. In this form, the reservoir body may be implanted subcutaneously into the fatty tissue under the skin surface, so that the spatial distance between the induction coil arrangement and a signal and energy supply unit to be provided extracorporeal is as small as possible, whereby good inductive coupling for an energy and signal transmission can be achieved.

An implantable reservoir body according to an embodiment of the invention gains a particularly high degree of independence and technical functionality when, along with the induction coil arrangement, a pump/electronics unit is provided within the reservoir body by which the working medium stored in the reservoir body can be metered and transferred in a controlled manner to a further implantable unit via a fluid channel. The pump/electronics unit, like the induction coil arrangement situated within the reservoir body, may be introduced free-floating into the reservoir volume enclosed by the elastic hollow body, or may be connected to or integrated into the hollow body wall of the reservoir body. Moreover, the battery unit may also be appropriately accommodated within the reservoir body.

As an alternative, an appropriate measure is to provide the pump/electronics unit outside the reservoir body, for example along a fluid channel leading out of the reservoir body and connecting the reservoir body to the unit to be implanted, so as to adequately inflate same with the working medium stored in the reservoir body. In this case, the pump/electronics unit should be encapsulated using a bio-compatible material. For example, further components can also be integrated into such a housing capsule formed separately from the reservoir body, such as a filling port for filling the reservoir body with the working medium or the battery unit for storing electrical energy.

In a preferred embodiment, the implantable reservoir body provides, in the area of its hollow body wall, a wall section formed as a type of adapter plate advantageously manufactured from a more stable or rigid material, as compared to the elastic hollow body wall. The adapter plate serves, on the one hand, for fixing the induction coil arrangement situated otherwise free-floating within the reservoir body, and also for a fixed passage of a fluid channel which either passes completely through the adapter plate or is attached to same at least on one side and opens into a valve-like connecting structure to which a transmission or fluid line leading further to the implantable unit can be adapted. The adapter plate can also be used as a directly connecting interface to further implantable components. For this purpose, mechanical connecting structures for adapting at least one further implantable unit are provided on the adapter plate. Apart from purely mechanical fastening structures, the adapter plate further comprises at least one electric connecting structure, so as to electrically connect a further unit to be implanted to a pump/electronics unit including a battery unit preferably provided within the reservoir body.

Alternative to or in combination with the adapter plate, one embodiment of the implantable reservoir body has a semi-circular or circular ring port for tapping the reservoir body and filling it with the working medium which preferably consists of a saline solution. The use of a gaseous working medium would also be conceivable. Also, a filling port parallel to the fluid channel could be provided to which it would be possible to adapt a filling line for the reservoir. Usually, reservoir bodies are implanted in an evacuated state and subsequently filled with a suitable working medium via a filling port.

In a particularly advantageous manner, the reservoir body consists of a preformed hollow body preferably made of a suitable polyurethane, the hollow body wall of which, during inflation and deflation, is subjected to a material compression or deformation at a largely constant hollow wall thickness, wherein the working medium can be injected into the evacuated and implanted reservoir body via the port described above, and the pump unit is transferred between the evacuated reservoir body and the unit to be further implanted. Thus, the inflation and/or deflation is mainly based on a material compression and deformation of the hollow body by a defined volume at a largely constant wall thickness, rather than on a material expansion as usually present in conventional compression bodies, e.g. manufactured from silicone. Apart from the low material stress, the advantage herein is the elimination of the initial strain resistance on the reservoir body, resulting in a hysteresis phenomenon for the pressure during the compression filling. This constellation in combination with the minimum dead space volume of the fluid channel resulting from the integrated system concept has a positive effect on the performance characteristics and the energy management of the pump unit to be used.

An implantable reservoir body configured according to the invention, which can be used in a modular manner in conjunction with units of different configurations to be implanted, will be described below in terms of specific exemplary embodiments without restricting the general idea of solution.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
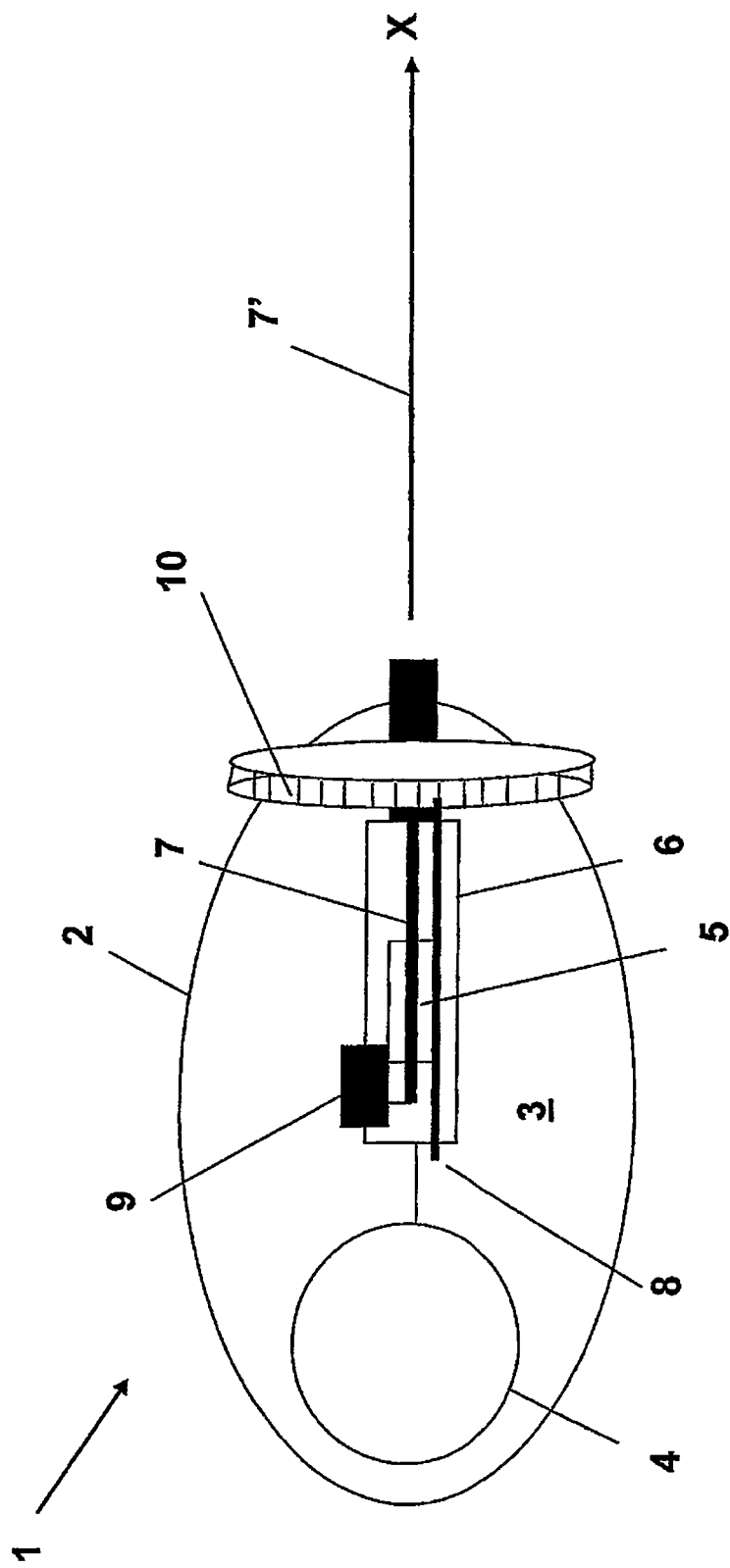
FIG. 1 is a schematic representation of a reservoir body configured according to an embodiment of the invention, including an integrated induction coil arrangement and an integrated pump/electronics unit.

FIG. 1 illustrates a greatly schematized reservoir body 1 configured according to an embodiment of the invention, which provides for a hollow body 2 enclosing a reservoir volume 3. Within the reservoir volume 3, which is enclosed by a hollow body wall of the hollow body 2 manufactured from a suitable polyurethane, an induction coil arrangement 4, a pump unit 5, an electronics unit 6, a fluid channel 7, and a filling port 8 are provided largely freely supported or free-floating. Alternatively to the free-floating supporting within the reservoir volume 3, at least the induction coil arrangement 4 can also be integrated into the hollow body wall of the hollow body 2. For preventing the components mounted inside the reservoir body 1 from taking any arbitrary positions, at least the pump unit 5 and the electronics unit 6 are provided to be placed on a common support substrate which is connected or fixed to the hollow body wall inside the hollow body 2 at a defined location. At the same time, the fluid channel 7 situated inside the reservoir body 1 and the filling port 8 lend themselves to be joined with the pump/electronics unit 5, 6 as a constructional unit. An intake protection 9 is provided in a particularly advantageous manner in the open intake area of the fluid channel 7, which serves to protect against blocking by a surface area present inside the hollow body 2.

Port conduit 8 is provided for filling the reservoir body 1 which, in conventional construction, can be connected to an external filling device via a planar tapping surface 10 or a convex or concave tapping surface 10 of circular or semi-circular shape. The tapping surface 10 may be provided with or without shaped tapping protection.

It is assumed that in the embodiment illustrated in FIG. 1 a battery unit is integrated into the electronics unit 6 which, as initially described, serves the purpose of energy storage by way of an electric charging process.

The reservoir body 1 illustrated in FIG. 1 thus represents a fully independently working drive unit for an implantable unit X which is operated using a working medium of preferably liquid or gaseous nature and therefore is connected to the reservoir body 1 via a fluid channel 7'.

Typically, the reservoir body 1 configured according to the invention serves for a controlled and metered supply of a working medium for inflatable as well as deflatable implantable units X, by which a controlled blocking of hollow organs, for example blood-, urea- or stool-conveying hollow organs, is possible. One preferred embodiment of such an implantable unit, for example, may be derived from German Patent DE 10 2004 018 807 B4 cited at the beginning.

Figure 2A:
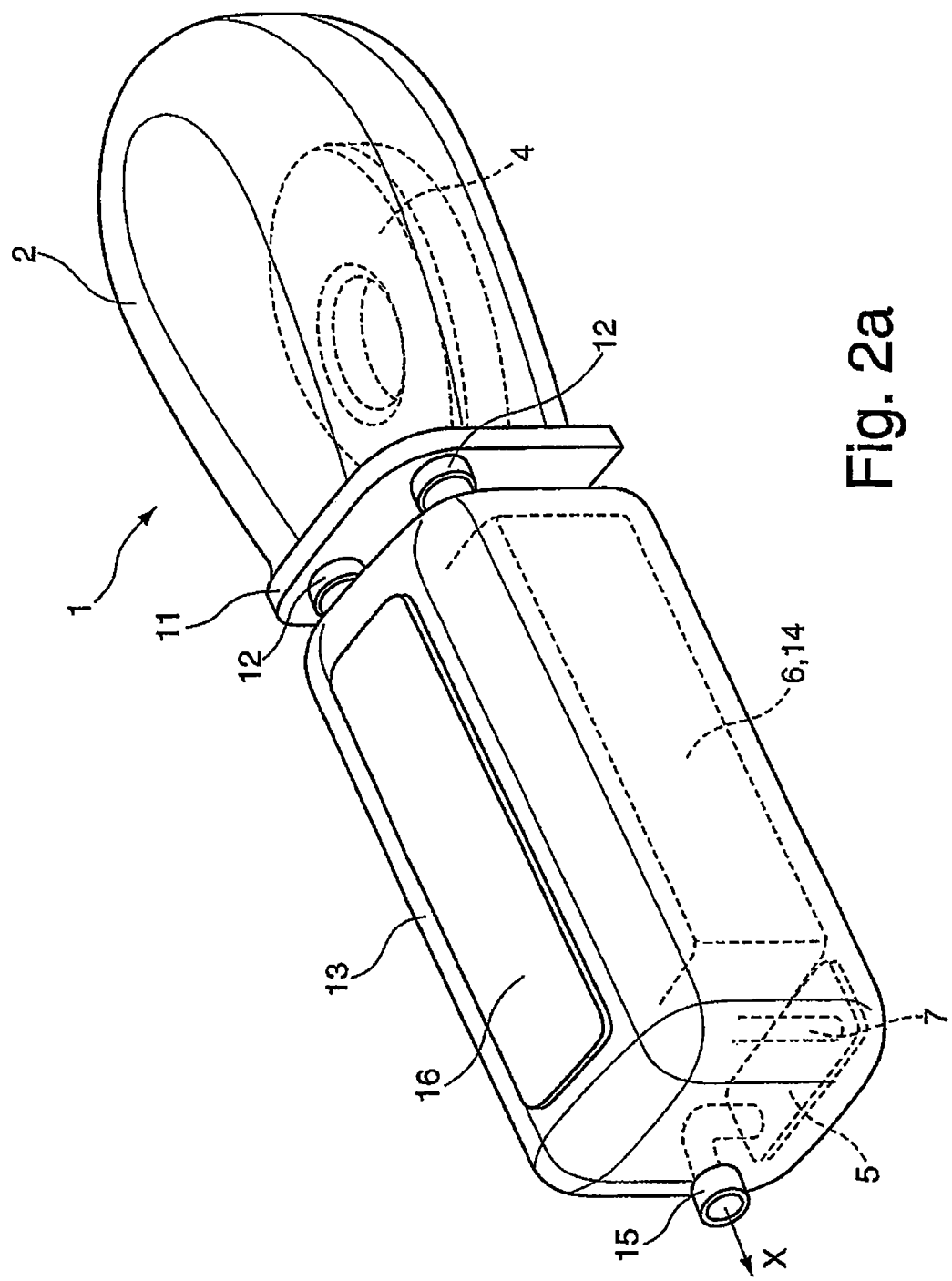
FIGS. 2a and 2b are perspective views, showing interior components with dashed lines, of an exemplary embodiment of a reservoir body with a pump/electronics unit connected via an adapter plate.
Figure 2B:
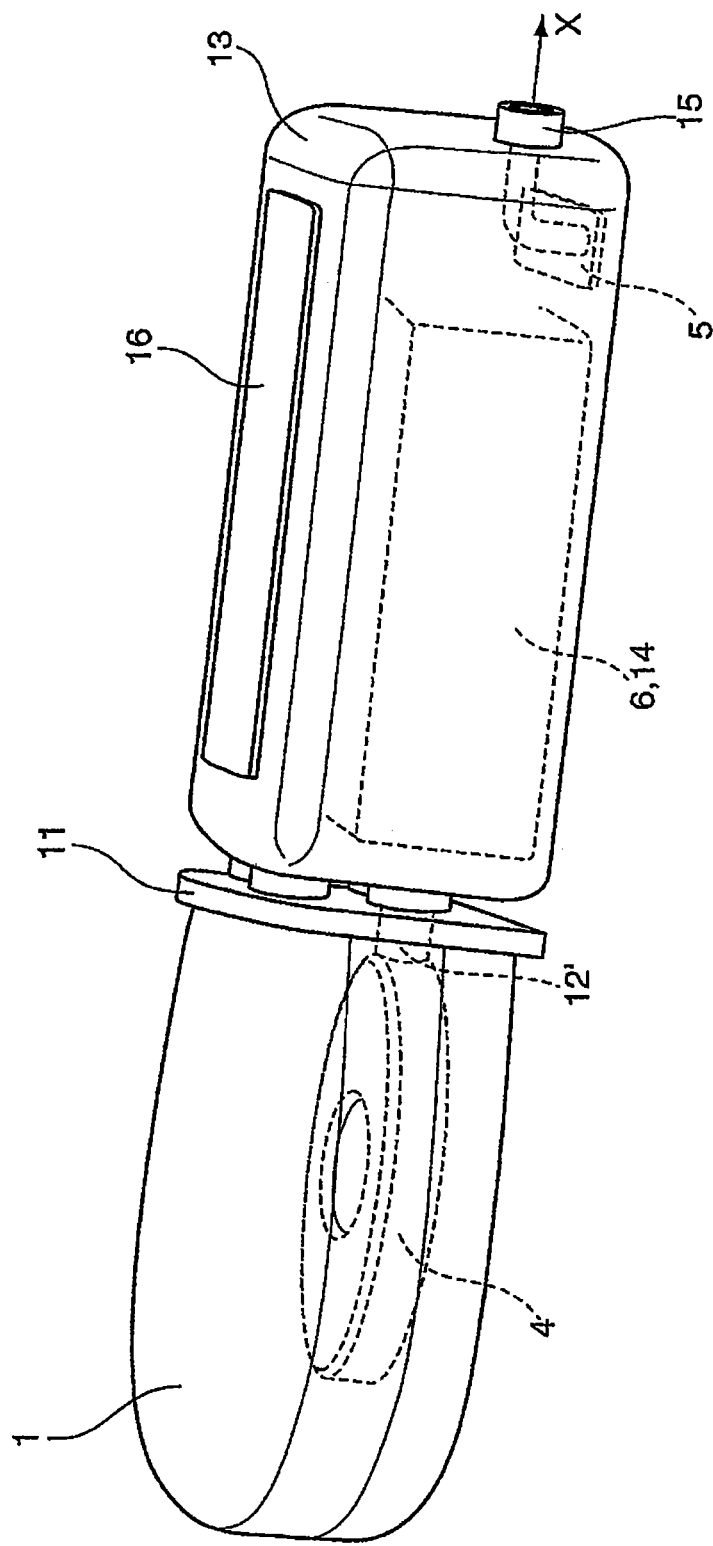

Differing from the exemplary embodiment illustrated in FIG. 1, the exemplary embodiment shown in FIGS. 2a and 2b comprises a reservoir body 1, into the reservoir volume of which only an induction coil arrangement 4 is introduced. The hollow body 2 of reservoir body 1 terminates in a fluid-tight manner at one side by an adapter plate 11 on which diverse connecting structures 12 are provided, via which a battery unit 14, the electronics unit 6 and the pump unit 5 integrated within the encapsulated housing 13 can be adapted. It can be seen from the exemplary embodiment as per FIG. 2b that the induction coil arrangement 4 is connected to a battery unit 14/electronics unit 6 integrated within the housing 13 via an electric connecting structure 12' and supplies a micropump unit 5 likewise integrated into the housing 13 with electric energy and respective control signals. The pump unit 5 is mounted within a fluid channel 7 connected to the reservoir body 1, the fluid channel 7 providing a connecting structure 15 at the output side to which an implantable unit X (not shown in more detail and to be supplied with the working medium stored in the reservoir body 1) can be connected. A surface port 16 is additionally provided at the upper side face of the parallelepiped housing 13 illustrated in FIG. 2b, via which the filling of the reservoir body 1 can take place.

The exemplary embodiment depicted in FIGS. 2a and 2b shows a simple configuration of a reservoir body 1 configured according to the invention, in which only an induction coil arrangement 4 is accommodated, which is connected to a pump/electronics unit 5, 6 provided outside the reservoir body 1, in order to basically supply same with electric energy which can be buffered or stored by a suitably provided battery unit. The adapter plate 11 illustrated in the exemplary embodiment serves for a modular connection to a housing structure 13, which ultimately comprises at least one fluidic connecting structure 15 for a connecting line to an implantable unit, for example a compression cuff for the controlled constriction of a hollow organ.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An implantable reservoir body for demand-oriented supply of a working medium serving at least for inflating at least one implantable unit (X) when the implantable reservoir body is connected to the implantable unit (X), the implantable reservoir body comprising:
   an elastic hollow body (2) having a wall which encloses a reservoir volume (3),
   an induction coil arrangement (4) within the reservoir volume (3), wherein the induction coil arrangement (4) is supported independently of the hollow body wall or is integrated into the hollow body wall or is mounted in fixed connection to a surface of the hollow body wall,
   a pump/electronics unit (5, 6) provided inside or outside the hollow body, the pump/electronics unit further being connected to the induction coil arrangement, and
   a fluid channel (7, 7') leading out of the hollow body (2) and connected to the pump unit (5) and/or adapted to be directly connected to the implantable unit (X) to be inflated.

2. The implantable reservoir body according to claim 1, wherein the hollow body (2) comprises an elastic preformed material which is subjected to deformation at a largely constant wall thickness during inflation and deflation of the implantable unit.

3. The implantable reservoir body according to claim 1, wherein the induction coil arrangement (4) is supported independently of the hollow body wall to be freely movable therein.

4. The implantable reservoir body according to claim 1, further comprising a wall section in an area of the hollow body wall being configured as an adapter plate (11), and
   a fluid channel (7, 7') passing through the adapter plate (11) or terminating at one side on the adapter plate (11) in a form of a fluid-tight connecting structure adapted to be connected to the implantable unit (X).

5. The implantable reservoir body according to claim 4, further comprising a mechanical connecting structure on the adapter plate (11) configured to adapt the implantable unit (X), and
   at least one electric connecting structure provided on the adapter plate (11).

6. The implantable reservoir body according to claim 1, further comprising a battery unit (14) provided inside or outside the hollow body, connected to the induction coil arrangement (4), and serving for energy supply of at least the pump/electronics unit (5, 6).

7. The implantable reservoir body according to claim 1, wherein the pump/electronics unit (5, 6) is configured as a constructional unit realized by microelectronic components and is mounted along or transversely to the fluid channel (7, 7').

8. The implantable reservoir body according to claim 1, wherein the fluid channel (7, 7') has an open conduit end situated inside the reservoir volume (3) which provides for an intake protection cap having a surface area present inside the hollow body for protecting against blocking.

9. The implantable reservoir body according to claim 1, further comprising an opening in the hollow body wall by which filling of the hollow body with a working medium takes place.

10. The implantable reservoir body according to claim 9, wherein the opening comprises a port (10) sealable in a fluid-tight manner and having a form of a planar or convex/concave tapping surface.

11. The implantable reservoir body according to claim 1, wherein the pump unit (5) and the electronics unit (6) are contained within the reservoir volume (3) separate from each other.

\* \* \* \* \*

UNITED STATES PATENT AND TRADEMARK OFFICE
CERTIFICATE OF CORRECTION

PATENT NO. : 8,545,385 B2
APPLICATION NO. : 12/937887
DATED : October 1, 2013
INVENTOR(S) : Hans-Juergen Schrag It is certified that error appears in the above-identified patent and that said Letters Patent is hereby corrected as shown below:

On the Title Page, Item (73):

The Assignee should be listed as:

-- Dritte Patentportfolio Beteiligungsgesellschaft mgH & Co. KG, Schönefeld/Waltersdorf (DE) --.

Signed and Sealed this
First Day of April, 2014

Michelle K. Lee
*Deputy Director of the United States Patent and Trademark Office*